United States Patent [19]

Lapeyre et al.

[11] Patent Number: 4,804,369
[45] Date of Patent: Feb. 14, 1989

[54] REMOVABLE HEAD FOR CONNECTION TO A PERCUTANEOUS PASSAGE

[75] Inventors: Didier M. Lapeyre, Pacy sur Eure; Jean P. Slonina, Le Vesinet, both of France

[73] Assignee: Biomasys Sarl, Precy-sous-Thil, France

[21] Appl. No.: 858,933

[22] Filed: May 1, 1986

[30] Foreign Application Priority Data

May 3, 1985 [FR] France ................. 85 06738

[51] Int. Cl.⁴ ............................... A61M 5/00
[52] U.S. Cl. ..................... 604/175; 604/43; 604/891.1
[58] Field of Search ............ 604/175, 51, 43, 52, 604/236, 237, 891, 905; 128/1 R; 251/149.1, 149.4, 346, 62, 129.11

[56] References Cited

U.S. PATENT DOCUMENTS

| 1,350,077 | 8/1920 | Loudon | 251/129.11 |
|---|---|---|---|
| 2,354,573 | 7/1944 | Brock | 251/129.11 |
| 2,759,570 | 8/1956 | Shirey | 251/62 |
| 3,052,444 | 9/1962 | Kintner | 251/62 |
| 3,972,506 | 8/1976 | Azuma | 251/129.11 |
| 4,092,983 | 6/1978 | Slivenko | 604/175 |
| 4,108,173 | 8/1978 | Slivenko et al. | 604/175 |
| 4,164,221 | 8/1979 | Bentley et al. | 604/175 |
| 4,328,948 | 5/1982 | Pearl, II | 251/149.4 |
| 4,350,175 | 9/1982 | Hoffa | 604/175 |
| 4,425,119 | 1/1984 | Berglund | 604/175 |
| 4,501,297 | 2/1985 | Baker | 251/129.11 |
| 4,654,033 | 3/1987 | Lapeyre et al., | 604/175 |
| 4,662,395 | 5/1987 | Strangfeld | 251/346 |

Primary Examiner—Stephen C. Pellegrino
Assistant Examiner—Ralph Lewis
Attorney, Agent, or Firm—Roland Plottel

[57] ABSTRACT

A removable head is provided for connection to an immovable percutaneous passage device giving access to a fluid circuit in a living organism, a fluid distribution housing and a system comprising this connection head and this fluid distribution housing.

Through the connection head of the invention a percutaneous passage, implanted in the blood network of a living organism, can be connected to an apparatus for treating the blood. It comprises a base, screwable on the percutaneous passage, forming a guide cylinder, for a tubular body through which are formed at least two channels. Means for actuating the head impart to the tubular body a translational movement which establishes in turn a direct flow between the channels then places them independently of each other in contact with the organism. The head of the invention further comprises safety devices and is motorizable.

19 Claims, 8 Drawing Sheets

REMOVABLE HEAD FOR CONNECTION TO A PERCUTANEOUS PASSAGE

BACKGROUND OF THE INVENTION

1. Field of the Invention

The present invention relates to a removable fluid exchange system, connectable to an immovable device for the percutaneous passage of fluids and atraumatic access to a fluid circuit, such for example as a blood or lymphatic circuit in a living organism.

The invention concerns more particularly the head for connection to the atraumatic access device, implanted in the living organism, and its fluid supply device.

The fluids which may be exchanged with a living organ are blood but also pharmaceutical products such as insulin, antibiotics, vasodilators. Hemodialysis is an important case of blood exchange concerned by the system of the invention.

All these fluids are extracted from or injected into the living organism by means of a removable atraumatic access device, which is formed by a valve system establishing at will communication between the inside and the outside of the living organism. The implantation of such an atraumatic access device is justified by the traumatism and sclerosis of the living tissues created by repeated injection using hypodermic needles when repeated treatment is necessary.

2. Description of the Prior Art

Devices for atraumatic access to an internal circuit of the organism are known. Most of them have in common the fact of comprising a body, a part of which is in direct connection with the fluid circuit of the organism and another part of which, isolated from the preceding one by a valve, is in relation with the external environment of the organism. This second part forms a well giving access to the fluid network of the organism, such as the blood, although this example does not form a limit to the application of the invention; it passes through the derm or true skin, emerges at the level of the epiderm and, outside the periods during which fluid exchanges are practiced, is closed by any liquid and bacteria tight means. In this access well is disposed a valve, formed either by an extensible membrane, or by a membrane which can be pierced by a needle, or by a ball or by any mechanical valve, or by a rotary drum or else by the truncated cone shaped body of a plug cock. Some of these access systems to the blood network will be discussed further on.

Whatever the type of valve, there still remains a cavity formed by the access well, when the plug of the atraumatic device is removed.

It is known that the connection of tubes, in which fluids flow, to an immovable atraumatic access device leads to difficulties of poor disinfection, poor rinsing, poor air draining because the open ends of the tubes themselves are handled in the open air before the operation, and because of the presence of a well giving access to the air.

Up to now, the operation for making the ends of the tubes and of the access well aseptic has been carried out manually using an antiseptic product but, since it is carried out in the air, it is partially inefficient.

Furthermore, the antiseptic products used in manual asepsy are poorly rinsed by the rinsing products, for example inside the ends of the tubes, or in certain concave parts of the access well.

The problem of blood coagulation when it is a question of exchanges with the blood network through the tubes is partially solved, in the prior art, by heparine injections as required. Bubble removal is provided, in some systems, by at least one bubble remover integrated in the treatment apparatus, a dialyzer for example. But these solutions are only suitable for the part of the system through which blood is removed from the organism. In so far as the part is concerned through which a liquid, blood or a medicament, is reinjected into the blood vessel, there is always the risk of having a little air remaining in the tubes or in the access well, before the tubes are connected to the atraumatic access device and before the valve is opened. There is always then the risk of injecting a little air into the blood circuit, which is very dangerous to the organism.

The injection, or exchange of fluids with a living organism is therefore a delicate operation, presenting risks and expensive because it is carried out by a highly qualified staff.

One object then of the present invention is to simplify and make reliable the operations for connecting an immovable percutaneous passage device to a connection head, connected by at least two tubes to its fluid supply device, itself connected to a treatment apparatus such as a hemodialyzer or an insulin injector for example.

Another object of the invention is to ensure the aseptisization, rinsing and bubble removal of the whole part of a system included between the valve of the atraumatic access device and the treatment apparatus, the valve being closed before the beginning of the treatment.

A further object of the invention is to allow the connection of the connection head to the atraumatic access device in non aseptic conditions, then in practicing asepsis, rinsing and bubble removal, without breaking the asepsis in the aseptisized zone, using controls external to this aseptisized zone, which controls may be manual but are preferably automated.

SUMMARY OF THE INVENTION

These objectives are reached with the system of the invention more particularly because of the design of the head connected to the device giving atraumatic access to the blood circuit. The head comprises a cylinder coaxial with an access well and pierced longitudinally with at least two passageways. The cylinder has at least one degree of freedom and moves by longitudinal translation in a base fixed to the atraumatic access device. In a first position of the cylinder, in which it is distant from the valve, there exists a free passage for the fluids between the end of a cylinder and the valve, which allows the flow of external fluids for aseptisizing, rinsing, and removing the bubbles from the tubes, the access well, in particular the internal walls, and the surface of the valve. The cylinder is further provided, at its end close to the valve, with means for opening this valve. These means are adapted for interrupting the passage of the fluids between the two passageways when said means are not in contact with the valve. In a second position of a cylinder, in contact with the valve, the cylinder opens the valve and establishes the fluid flow between the living organism and at least one passageway bored in the cylinder without any part having been exposed to the air. The parts which have been aseptisized therefore remain aseptisized.

In other words, when the cylinder in the connection head is in a position remote from the valve, there is free flow of all the external fluids required for preparing the treatment operation. When the cylinder is in a position in contact with the valve there is an exchange of fluids between the living organism and the outside, through aseptisized equipment.

The cylinder is moved, with respect to the body of the connection head, by mechanical, fluid (air or liquid) or electric means.

Safety devices control the position of the valve and prevent any injection of aseptisizing products in the living organism.

Of course, the assembly formed by the connection head and the fluid supply device is designed so as to avoid any cavity, so as to prevent the coagulation of blood when this liquid is concerned.

More precisely, the innovation concerns a removable head for connection to an immovable percutaneous passage device giving access to the blood circuit or similar of a living organism, this percutaneous passage comprising an access well formed by a hollow cylindrical body having a valve at one end and a threaded portion at another, this connection head further comprising:

means for fixing it to the removable device, these means being formed by a base whose central part of extra thickness, is screwable onto the hollow body and is pierced, forming a guide cylinder coaxial with the hollow body, means for fluid exchange with the blood circuit or other fluid formed by: a tubular body fitting snugly into the guide cylinder, said tubular body being pierced over the whole of its length by at least two channels opening into the access well, which places them in communication and a connection piece, integral with the tubular body, providing the connection between each of the channels and an external connection tube, means for actuating the head formed by an actuator which communicates to the tubular body, through the connection piece, at least a longitudinal translational movement, means for operating the valve, said means, carried by the end of the tubular body close to the valve, further providing interruption of the communication between the channels when the tubular body is in contact with the valve and when this latter, open, is in communication with the blood circuit.

BRIEF DESCRIPTION OF THE DRAWINGS

The invention will be better understood from the detailed description of some embodiments, this description referring to the accompanying Figures which show.

DESCRIPTION OF THE PREFERRED EMBODIMENTS

Figure 1:
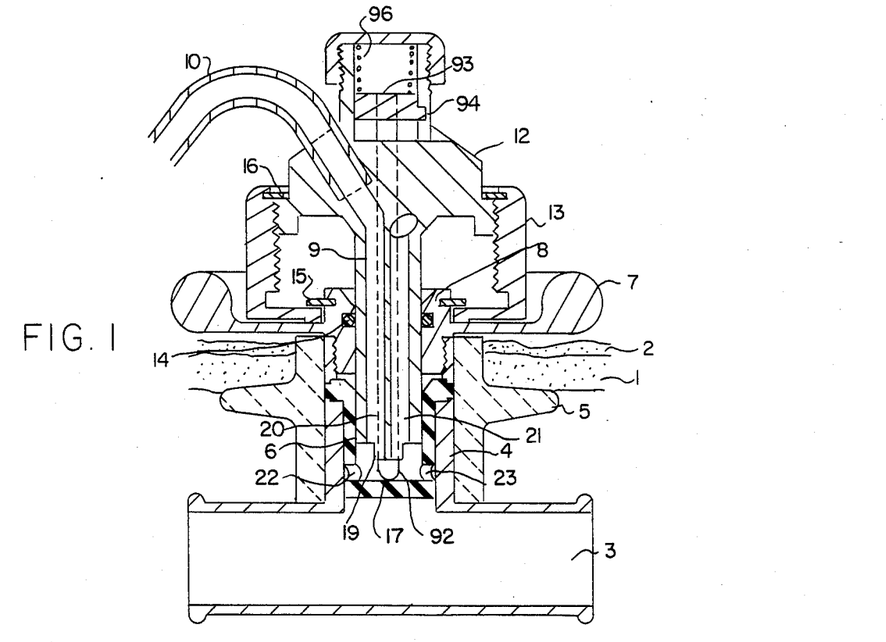
FIG. 1 is a sectional view of a first embodiment of the connection head of the invention mounted on an atraumatic access device in the closed position of the valve, FIG. 2 a sectional view of the connection head of FIG. 1, the valve being in the open position, FIG. 3 a sectional view of the connection head, through a plane orthogonal to that of FIG. 2, the valve being in the closed position, FIG. 4 a top view of the connection head of FIG. 1, FIG. 5 a sectional view of the first embodiment of a connection head of the invention adapted to a second type of percutaneous passage valve, the valve being in the closed position, FIG. 6 a sectional view of the first embodiment of the connection head of the invention, adapted for injecting medicamentous fluids into the living organism, with the valve in the closed position, FIG. 7 a diagram showing the use of electric actuation in the first embodiment of the connection head of the invention, FIG. 8 a sectional view of a second example of the connection head of the invention, in the case of air or liquid fluid actuation, FIG. 9 a diagram showing the connection between the internal channels and the external tubes in a third example of connecting piece 9 according to the invention, the type of actuation, fluid, mechanical or electric not being shown, FIG. 10 a diagram showing the connection between the internal channels and the external tubes in a fourth example of connecting the piece 9 of the invention, the type of actuation, mechanical or electric, not being shown, FIG. 11 a top view corresponding to FIG. 8, FIG. 12 an elevational view of the form of the connection grooves in the case of the second example of the connection head of the invention, FIG. 13 a diagram showing the use of mechanical actuation in the case of a second example of a connection head of the invention, FIG. 14 a diagram showing electric actuation in the case of the second example of the connection head, FIG. 15 a sectional view of the second example of the connection head in the case of a fluid actuator, FIG. 8 showing a safety system in the flow of fluids dangerous for the living organism, FIG. 16 a top view of the safety system of the preceding Figure, FIG. 17 a simplified diagram of a treatment system comprising a connection head and a fluid distribution housing in accordance with the invention, and FIGS. 18 and 19 a sectional schematical view of a distribution housing without useless spaces, harmful in accordance with the invention.

FIG. 1 shows a sectional view of a first embodiment of a remarkable connection head according to the invention, mounted on a known atraumatic access device, described in U.S. Pat. No. 4,654,033.

The invention will be better understood by recalling first of all the structure and operation of a device giving atraumatic access to a fluid circuit ibn a living organism, which will be designated by removable "percutaneous passage" hereafter, so as to simplify the language. In the same spirit, a blood circuit will be considered which is one case of a fluid circuit in a living organism.

The percutaneous passage is implanted in the organism under the derm 1 and the epiderm 2. It comprises a T connection, the two aligned parts of which form a tube 3, at the ends of which are fixed short artificial flexible blood pipes sutured respectively to a vein and an artery. All that in the non limitative case of an arterial-venous shunt.

The third part of the T forms a hollow body 4 which connects the surface of the epiderm 2 to the tube 3 through which the blood flows. For anchoring the percutaneous passage in the tissues of the organism, the hollow body 4 is integrally formed with a ring 5 having at least one collar. Ring 5 is made from carbon impregnated carbon fibers which confers thereon a porous structure: by colonizing the pores of the rings 5 the tissues ensure fixing of the percutaneous passage in the organism, thus making it immovable.

The valve which controls the blood or fluid exchanges between the inside of the living organism and the outside is here formed by a body 6, in the form of a piston inside the hollow body 4, with which it provides good sealing. This piston 6 is made from an elastomer material and is fixed by one of its ends in the hollow body 4, whereas its other end, closed, is at the level of the wall of tube 3 but does not penetrate in tube 3 when the valve is closed. Thus, the internal wall of the hollow body 4 closes two openings 22 and 23 formed in the cylindrical wall of piston 6.

To open the valve, the elastomer piston 6 must be deformed by extending it. Its end close to tube 3 then penetrates therein which results in freeing the openings 22 and 23 and establishing a blood or fluid flow between the blood vessels, through tube 3, and the outside of the organism. With appropriate means the flows are separated and one opening, 22 for example, is used for removing the blood and the other opening, 23 in this case, is used for reinjecting blood and/or pharmaceutical liquids. The valve is shown open in FIG. 2.

The hollow body 4 finally comprises, on the side of its end external to the organism, a threaded portion which allows a plug to be fixed when the percutaneous passage is not used, or a connection head when it is used for fluid exchanges with the blood network.

The percutaneous passage has then an access well, formed by the inside of the hollow body 4 and piston 6: this access well must be disinfected and rinsed before the blood treatment operation. This is one of the functions fulfilled by the connection head of the invention shown in FIG. 1.

This head comprises essentially a base 7 fixable to the hollow body 4 of the percutaneous passage. Any known mechanical fixing means may be used for fixing base 7 to body 4, as long as it provides good sealing and a registered position of the base with respect to the body, but a threaded portion is the preferred means since it is the least traumatic for the patent and exerts the least force on the percutaneous passage.

This base comprises on its periphery a collar which serves for screwing it into the hollow body 4 and, in its central part, an extra thickness having at its center a bore coaxial with the hollow body 4. This passage is machined accurately so that it forms a guide cylinder 8. In addition, it has an inner diameter equal to the inner diameter of the elastomer piston 6.

In guide cylinder 8 is fitted a tubular body 9, which may move with one degree of freedom along the axis common to the hollow body 4, piston 6 and the guide cylinder 8. This tubular body 9 is pierced longitudinally preferably along a diameter by at least two channels 20 and 21. In fact, even in the case where the percutaneous passage is used only for injecting a product into the blood, a second channel is required for allowing flow of the aseptisizing and rinsing liquids, as well as for removing bubbles during preliminary operations.

Channels 20 and 21 communicate at one end of the tubular body 9 with the treatment equipment through tubes 10 and 11. They emerge at the other end of the tubular body 9. Said end comprises means for operating valve 6, under the double condition of leaving free flow of fluids between channels 20 and 21 when the valve is closed and isolating the same channels when the valve is open. These means are variable depending on the type of valve used.

Figure 2:
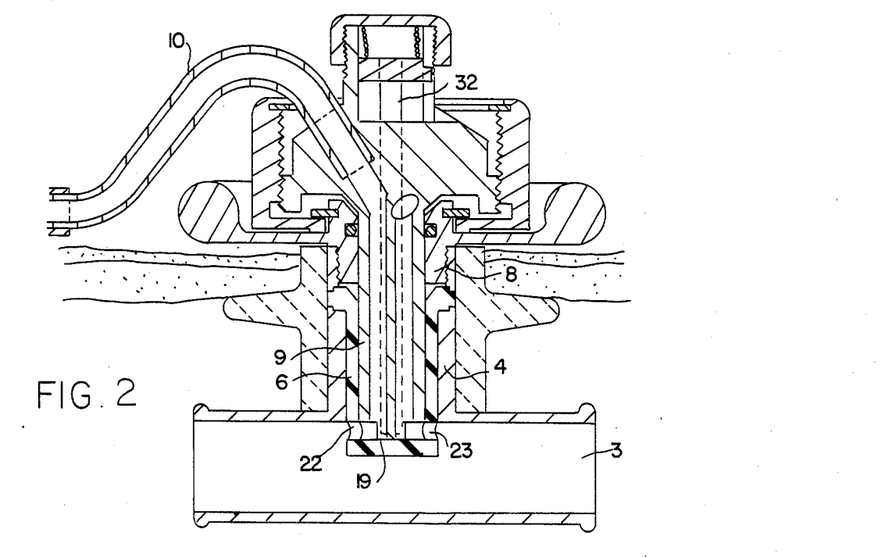
Figure 3:
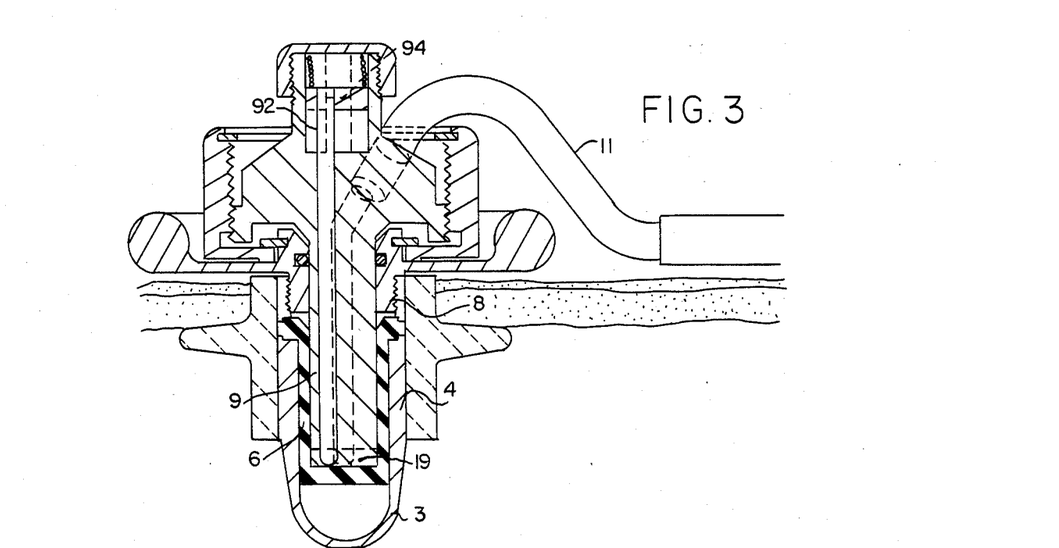

In the case of the valve described in U.S. Pat. No. 4,654,033 in the name of the applicant, which valve requires elongation for being opened, the means for opening it is formed by a projection 19 on the tubular body 9. This projection 19 has a length—measured along the axis of movement of the tubular body 9—substantially equal to the diameter of the openings 22 and 23 in the elastomer piston 6, so as to allow regular flow of the blood between openings 22 and 23 in channels 20 and 21, respectively without any risk of coagulation of the blood in a cavity not swept by the blood flow, as is clear from FIG. 2. Moreover, projection 19 is formed, in the present case of an elastomer valve, by a portion of the tubular body 9 forming a flange along a diameter perpendicular to the diameter carrying the two channels 20 and 21. FIGS. 1 and 2 show this flange in its thickness, whereas FIG. 3 shows it in its width, that is to say in the axis of the two openings 22 and 23.

The tightness to fluids and bacteria of the percutaneous passage-connection head assembly is provided by:

the slightly forcible insertion of piston 6 in the hollow body 4 and its positioning by means of a groove, the snug fit between the outer surface of the tubular body 9 and the inner surface of piston 6, a seal 14 between the guide cylinder 8 and the tubular body 9, the bearing relation of piece 7 on the top of cylinder 4.

The function and use of other parts shown in FIGS. 1, 2 and 3 will be explained and discussed subsequently, as well as the adaptation of the connection head to other types of valves.

The operation of the connection head of the invention will be readily understood from FIGS. 1, 2 and 3.

In FIG. 1, the tubular body 9 is in a position remote from valve 6: to simplify the language, this position will be called "high" position. There exists a communication between channels 20 and 21, inside piston 6, for the flange 19 cannot come into contact with the flat wall of piston 6. The valve is therefore closed. It is then possible to introduce an aseptisizing fluid through a tube, 10 for example, then to rinse using distilled water or physiological serum. The removal of bubbles takes place simultaneously and all these fluids—as well as the bubbles—are removed through the second tube, 11 in this case. The whole of the parts which were not aseptic, and which will be subsequently in contact with the blood, are thus aseptisized.

In FIG. 2, and without the connection head being removed or exposed to the air, the tubular body 9 has undergone a translational movement along its axis; it is in contact with valve 6, which it extends. This position will be called "low position". The means by which the tubular body 9 has undergone a translational movement will be explained subsequently. In this low position, with the valve open, the openings 22 and 23 of piston 6 are in communication with channels 20 and 21, respectively, whereas flange 19 provides sealing with the bottom and the internal wall of piston 6, as is shown in FIG. 3. In this case, the blood may leave the percutaneous passage for example through opening 22 and channel 20 and be reinjected, after treatment, through channel 21 and opening 23.

At the end of the treatment, the tubular body 9 is brought back to the high position, which closes valve 6 again and interrupts the blood exchange. The whole of the tubes and the connection head may then be swept with blood and washed by means of adequate fluids since communication between channels 20 and 21 is re-established. After rinsing, at the end of treatment, the connection head is unscrewed and the percutaneous passage is closed by a threaded plug.

Figure 4:
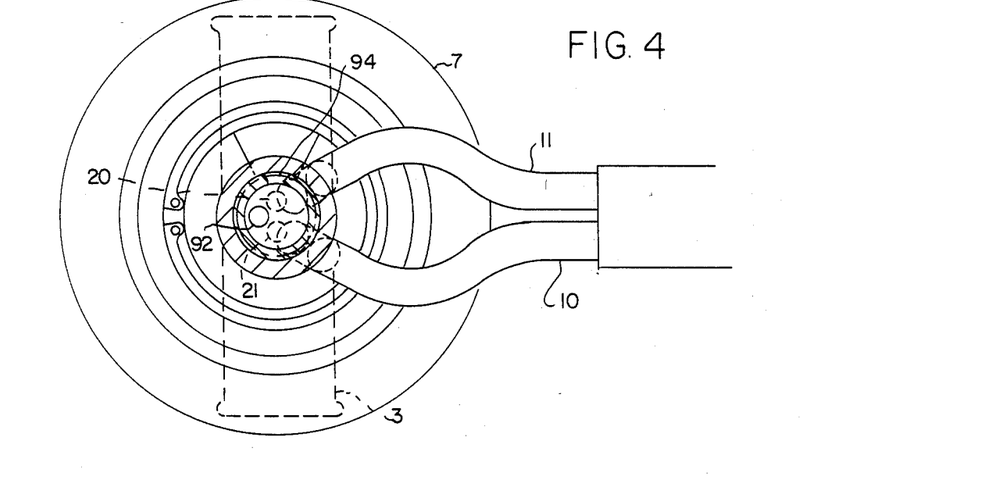

FIG. 4 completes the sectional FIGS. 1 to 3:

Its top view shows the two external tubes 10 and 11 which places channels 20 and 21, formed through the tubular body 9, in communication with the initial part of the treatment system, said initial part being formed by a housing for supplying different fluids—the term supplying being interpreted in its widest sense, that is to say not only the arrival but also the removal of fluids.

Figure 5:
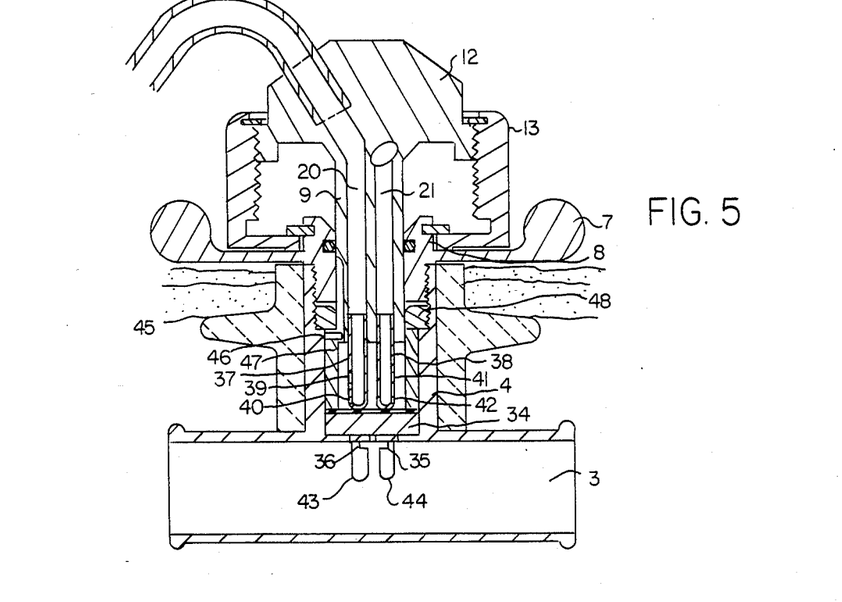

FIG. 5 shows one method of adapting the connection head of the invention to a second known type of percutaneous passage valve.

This valve is formed by a thick elastomer membrane 34 held against the wall of the blood take-off tube 3 by means of a sleeve 47 concentric with the hollow body 4, and a threaded ring 48. The membrane 34 is pierced with at least two series of star shaped slits formed along the axes 35 and 36. In the absence of any stress the lips of the slits are closed and membrane 34 is sealed, at the low pressures considered: the valve is closed.

For opening the valve two hypodermic needles or tubes 37 and 38 are pushed through the membrane 34, whose slits open elastically. Openings formed in the wall of tube 3 correspond to the position of the slits. Preferably, for avoiding clogging with elastomer particles, the tubes are rounded at their ends and they comprise a series of openings such as 39 and 40, 41 and 42 along a generatrix. FIG. 5 shows the valve in the closed position, and the connection head in the high position. When the valve is open and the connection head in the low position the tubes assume the position 43–44 shown with broken lines.

The connection head of the invention still comprises a base 7 fixable to the blood take-off T and an extra thick part 8 forming a guide cylinder, in which moves a tubular body 9 comprising two channels 20 and 21 bored in a longitudinal direction.

Tubes 37 and 38 which form an integral part of the valve are fixed in channels 20 and 21 by any suitable means.

The means for opening the valve is formed by the cylindrical body 9 itself, which pushes the tubes 37 and 38 through the membrane 34.

The means for interrupting the flow of fluids between channels 20 and 21, when the valve is opened, is formed by the lower flat end of the cylindrical body 9 which comes into contact with the flat surface of membrane 34.

The operation of the connection head of the invention is identical in the case of FIG. 5 with that of the preceding Figures. In the high position, with the valve closed, the antiseptic and rinsing fluids sweep and remove the bubbles from the external tubes, and a first channel 20 and leave through the openings 39, 40 and sweep the inner volume of sleeve 9 and leave through channel 21 via openings 41 and 42. All the surfaces are therefore aseptisized and rinsed. The valve is opened, without any part being exposed to the air, by a translational movement to the low position of the cylindrical body 9: the blood may then leave the organism for example through openings 39, 40 tube 37 and channel 20 and be reinjected after treatment through channel 21, tube 38 and openings 41, 42.

Contrary to the other cases described in which the angular position of piece 9 requires very approximative positioning which is achieved by approximately orientating tubes 10 and 11 on the outside, the case of FIG. 5 requires precise orientation of piece 9. Tubes 37 and 38 must in fact pass exactly through the axes 35 and 36. This is achieved by means of groove 45 and stud 46.

Figure 6:
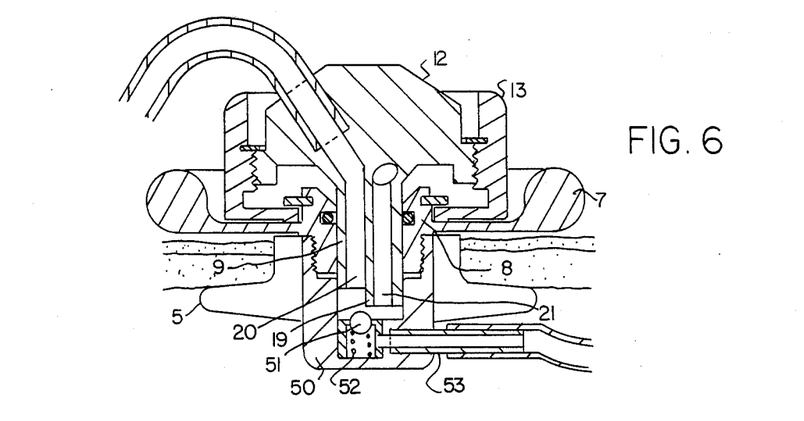

FIG. 6 shows another adaptation of the connection head of the invention to a third type of one way percutaneous passage, intended for example for injecting a medicament such as insulin into the organism at regular intervals.

The percutaneous passage is in this case modified with respect to those which have been described up to now. A collar 5, made from a carbon-carbon composite, fixes under the derm 1 and epiderm 2 a hollow body 50 whose bottom comprises a valve closed by a ball 51, pushed against its seat by a spring 52. This valve, normally closed in the absence of any external force, opens into a passageway 53 connected to a blood vessel for example. The hollow body 50 comprises, like the hollow body 4 situated in the blood take off Ts a threaded portion for fixing thereto either a plug or a connection head.

The connection head of the invention still has the same structure which will not be described again in detail: base 7 and guide cylinder 8, tubular body 9 formed longitudinally with two channels 20 and 21.

The means for operating the valve is, as in the case of the preceding Figures, formed by a projection 19 on the tubular body 9. The material which forms this projection completely surrounds a channel, 21 for example, so that this latter is extended with respect to the other channel. In addition, this projection 19 is partially straight above ball 51: when the cylindrical body 9 is in the low position, the projection pushes ball 51 and spring 52 back and the valve is opened.

The means for interrupting the flow of fluids between channels 20 and 21 is also the projection 19 which surrounds one of the two channels, 21 for example. In other words, channel 21 is longer than channel 20 and ends in a flat surface parallel to the surface of the bottom of the hollow body 50. When the cylindrical body 9 is in the low position, the end of channel 21 is in continuous contact with the surface of the bottom of hollow body 50 and channel 21 is closed.

It will be readily understood that, when the cylindrical body 9 is in the high position, the valve is closed and communication between channels 20 and 21 allows aseptisization and rinsing of all the surfaces previously non aseptic. When the cylindrical body 9 is in the low position, one of the two channels, 21 in the example, is closed, the valve is open and the injection of a pharmaceutical product into the blood circuit may take place. Up to now, the means by which the connection head is actuated and the cylindrical body 9 driven with a translational movement along its main axis, have not been explained. These means are multiple.

Referring again to FIGS. 1, 2 and 3, a first mechanical and manual means for causing longitudinal translation of the cylindrical body 9 is shown.

This means comprises on the same side as its end external to the living organism a part 12 of a shape adapted for providing connection of the inner channels 20 and 21 with the external tubes 10 and 11 through two metal end pieces.

This first part 12 connecting between tubes, which is therefore integral with the cylindrical body 9 and machined from the same block of material, comprises, on its largest diameter circumference, a threaded portion to which an operating nut 13 corresponds.

By rotating the operating nut 13, the connecting part 12 moves along the threaded portion, communicating thereby a translational movement to the cylindrical body 9. The operating nut 13 has a fixed position, with respect to the longitudinal axis of the connection head, because it bears on base 7 and because a washer or circlip 5 prevents it from translating along this axis.

The length of the threaded portion of the operating nut 13 is equal to the length of the possible translational movement of the cylindrical body 9, without damage to the elastomer valve 6.

Another washer or circlip 16 prevents the connection part 12 from leaving the threaded portion.

Of course, any mechanical means other than the one shown in FIGS. 1 to 3 belongs to the scope of the invention. For example, the translational movement towards the so called high position (valve closed) may be provided by a coil spring bearing on the facing faces of base 7 and the connecting part 12, whereas the translational movement to the low position (valve open) results from the action of a cam engaging with a stirrup which replaces the operating nut 13 and counteracts the action of a spring, by pushing on the connecting part 12.

Figure 7:
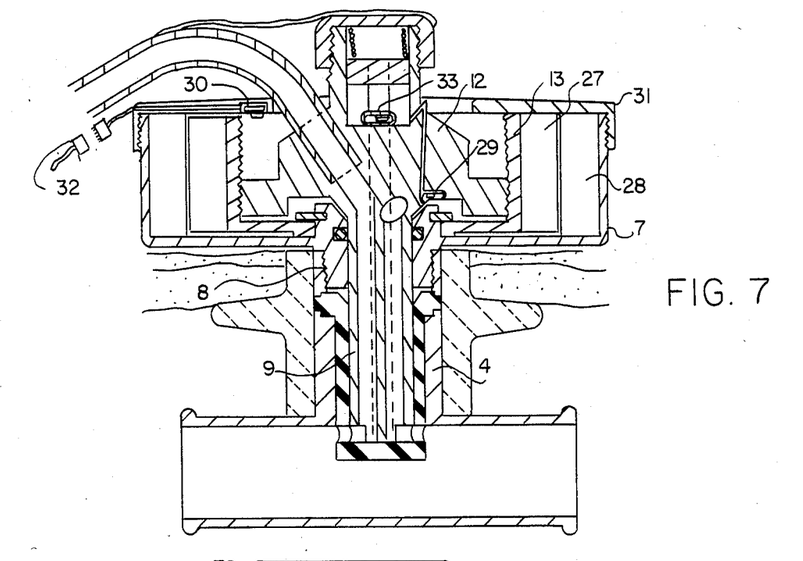

FIG. 7 shows another means of actuating the connection head of the invention. It is a question of an electric motor which is preferably controlled by a sequencer of an apparatus for automating the treatment operations.

The base 7 of the connection head is, in this case, of a slightly different shape and it supports, on its external ring, an electric motor stator 28, fed with conducting wires through a connector 32.

The operating nut 13 also has an adapted shape and it is integral with a rotor 27 forming, with stator 28, the electric motor. The threaded portion carried by the operating nut 13 is in this case of a smaller pitch than the pitch of the mechanical means, so as to serve as gearing down means so that the translational movement is not abrupt.

The connecting part 12 is of the same type as that of the mechanical means, but its threaded portion is of course adapted to that of the operating nut 13.

Two electric contacts 29 and 30, placed at the end of travel of the connecting bar 12, control the movement of the cylindrical body 9: when the connecting part crushes one of these contacts 29 or 30, it thus interrupts the passage of the electric current into the motor 27, 28 which is of course rotatable in both directions. The end of travel contact 30 in the high position may for example be provided on the lid 31 of the case of the motor.

The bearing for the rotor 13+27 may be very rudimentary and be formed by the friction of piece 13 made from PTFE Teflon on the metal piece 7. However, a ball bearing could also be used at the same position.

Figure 8:
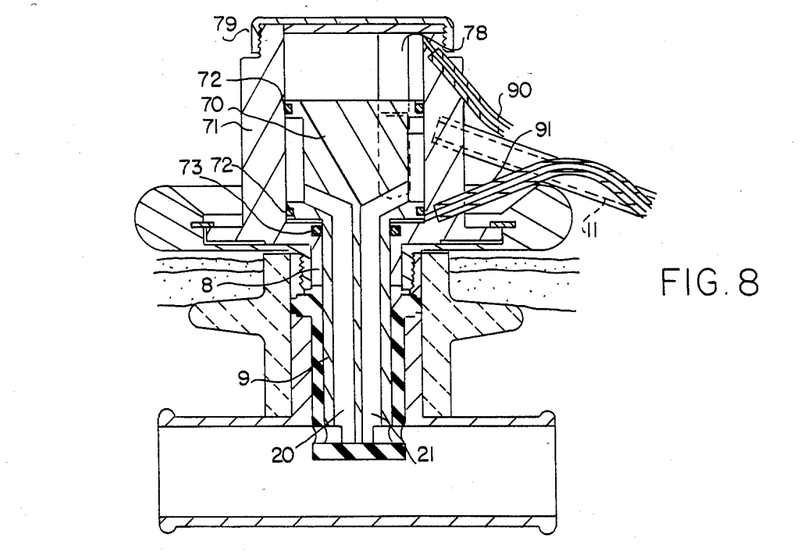

FIG. 8 shows a second embodiment of the connection head of the invention which is also used in FIGS. 11, 12, 13, 14, 15 and 16. This FIG. 8 describes actuation by fluid pressure (air or liquids).

The connection head still comprises a base 7, required for fixing the head to the percutaneous passage, but the guide cylinder 8 is in this case fixed to a cylinder 71 of the fluid actuator. The tubular body 9 is integral with a piston 70 which moves in the cylinder 71 of the actuator, closed by cover 79.

The drive fluids—air or liquid—are introduced through pipes 90 and 91 and act respectively between the upper face of piston 70 and cover 79, whose threaded portion comprises a sealing product and between the lower face of piston 70 and the upper face of a guide cylinder 8.

Seals 72 on the piston 17 of the actuator and 73 on the guide cylinder 8 prevent the drive fluids from being mixed with the blood or pharmaceutical fluids which flow through the connection head.

Figure 9:
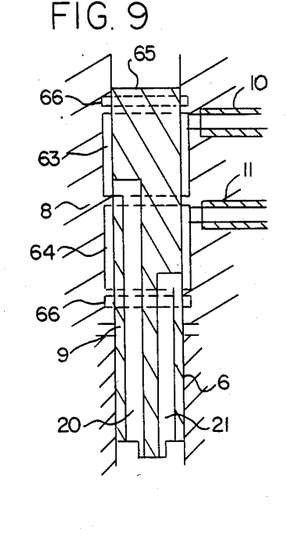
Figure 10:
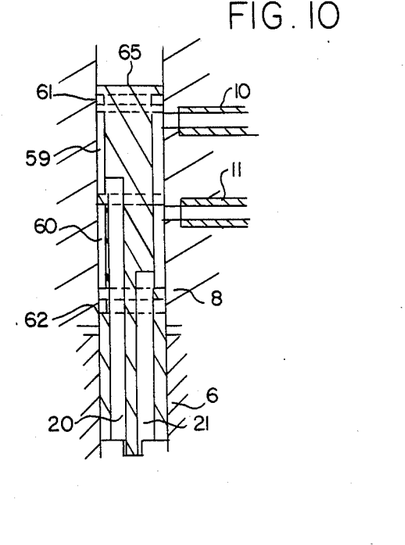

Because part 12 for connection to the external tubes 10 and 11 is, in the case of FIG. 8, i.e. the second example of the connection head of the invention, completely surrounded by cylinder 71 of the fluid actuator, it is necessary to adapt accordingly the connection of channels 20 and 21 to the external tubes 10 and 11. FIG. 8 shows one example of it, which is not limitative. FIGS. 9 and 10 which show other embodiments of the method of connecting piece 9 in fact show other possibilities. In them, only the parts concerned by the connection of the fluids are shown so as to simplify the Figures. The actuation means could be the same as those already described.

FIG. 9 shows the tubular body 9, a part of the elastomer valving body 6 and a part of the guide cylinder 8. This latter forms a cylinder in easy fit contact with the tubular body 9. In the internal wall of the guide cylinder 8 are formed two cylindrical recesses 63 and 64 which are in communication, at the first end, with channels 20 and 21 respectively and at their second end with the external tubes 10 and 11 respectively. The length of grooves 63 and 64 is equal to the length of the translational movement of the tubular body 9 and their section is in harmony with the section of channels 20 and 21, or tubes 10 and 11, so as not to present any resistance to the passage of blood. These grooves 63 and 64 therefore allow a continuous flow of the fluids from the percutaneous passage to the outer tubes 10 and 11 whatever the position, high or low, of the tubular body 9. Scraper seals 66, situated above and below the two grooves, ensure sealing of the two connections. The upper face 65 of the cylindrical body 9 may be in relation by any means known to one skilled in the art, either with a mechanical actuator, or with an electric actuator or with a fluid actuator.

FIG. 10 shows a variant of this method of connection by grooves but, whereas in the example of FIG. 9, the tubular body 9 has a smooth external wall and the cylindrical recesses are formd in the guide cylinder 8, in this variant it is the guide cylinder 8 which has a smooth internal wall and cylindrical recesses 59 and 60 are formed in the tubular body 9. Seals 61 and 62 provide sealing between the parts through which the blood flows and the external environment of the connection head.

Should a slight leak occur between grooves 59 and 60, or 63 and 64, following insufficient meeting between tubular body 9 and guide cylinder 8, it would not have serious consequences for it is the same fluid, blood for example which flows through these grooves.

It will be noted that in the case of FIGS. 9 and 10 the circular recesses 59, 60, 63, 64 in the piston or the cylinder could be grooves parallel to the axis of the system, but that, in this case, it would require rotational immobilization of the sliding stud 78 type shown in FIG. 8.

FIGS. 9 and 10 are in fact generalization Figures. In actual fact it is not advisable for the cylindrical recesses 59 and 60 or 63 and 64 to be toric and coaxial with the tubular body 9, for that would risk causing poor sweeping by the fluid which flows through them, between the orifice of a channel, 20 or 21, and the orifice of a tube, 10 or 11, and coagulation of the stagnant blood.

Figure 11:
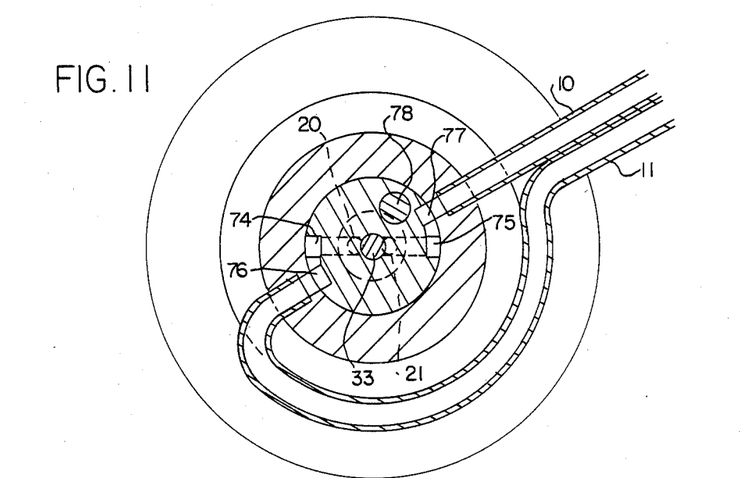
Figure 12:
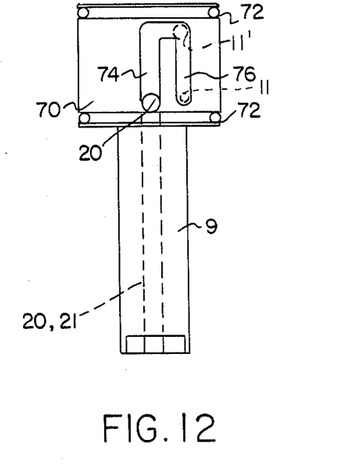
Figure 13:
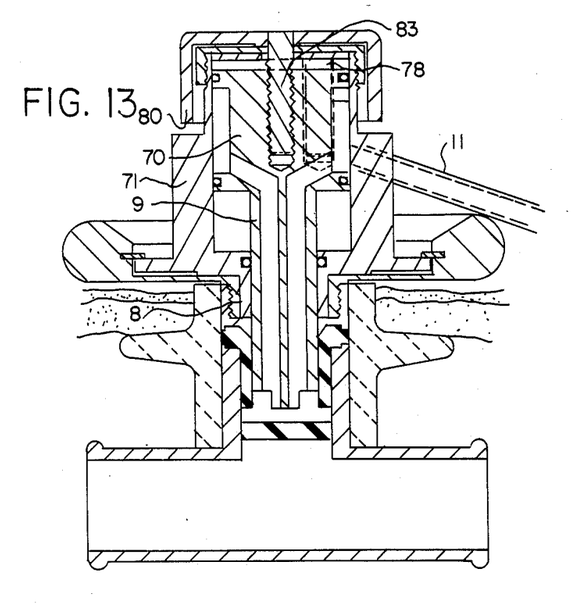

This is why these grooves are in the form of a U, which can be clearly seen in FIGS. 11, 12 and 13. FIG. 11 is a top view, in section, of the connection head of FIG. 13, whereas FIG. 12 is an elevational view of the tubular body 9 showing one of the U shaped grooves, the other being symmetrical and hidden by the body.

In FIG. 11, it can be seen that the grooves 74–76 and 75–77 do not completely surround the tubular body 9. On the other hand, they are at the same level and preferably diametrically opposite.

FIG. 12 shows the U shape of a groove. Each groove 74–76 or 75–77 is formed of a longitudinal portion 74, at the base of which emerges a channel, 20 for example, then a transverse portion, which communicates with a second longitudinal portion 76. The two portions 74 and 76 have a length equal to the translational length of the cylindrical body 9. The outer tube 10 for grooves 75–77 and tube 11 for grooves 74–76 open into grooves 77 and 76 respectively.

When valve 6 is closed and the tubular body 9 is in the high position, the outer tube 11 opens into the low part of groove 76: the aseptisizing fluid and the rinsing fluid sweep the whole of grooves 74, and 76 and remove the bubbles therefrom.

When the tubular body 9 is in the low position, and valve 6 is open, tube 11 opens, see FIG. 12, into the high part of groove 76 at 11': the blood flows through the grooves 74 and 76. Groove 76 in this case forms a cul-de-sac but that is not a disadvantage since the last operation for introducing blood was to rinse with the physiological serum: groove 76 is therefore filled with physiological serum without danger for the organism and without the risk of coagulation.

This form of groove explains and justifies the form of the tubular body and its connection part 70, in FIG. 8, having a fluid actuator or in FIGS. 11 to 16.

FIG. 13 further shows, like FIG. 8, a connection head of the invention in the second embodiment but in the case of FIG. 13, the mode of actuation is mechanical instead of being hydraulic.

Since the external tubes 10 and 11 are no longer connected to the end of the tubular body 9, through a connecting piece 12, as was the case in FIG. 1, it becomes possible to install a manual or automated axial mechanical actuator. This comprises an operating nut 80, comprising a threaded shaft 83 which cooperates with a threaded portion in the connecting piece 70. A cover screwed on piece 71 immobilizes the operating nut 80 longitudinally through a collar situated at the base of the threaded shaft 83. This shaft 83 is welded to nut 80 after having imprisoned the cover. Using passage holes not shown 71 is screwed to the top of nut 80.

A stop 78 sliding in piece 70, also shown in FIGS. 8 and 11, prevents the tubular body 9 from rotating when the operating nut 80 is screwed or unscrewed and always keeps channel 11 facing groove 76 and channel 10 facing groove 77.

Figure 14:
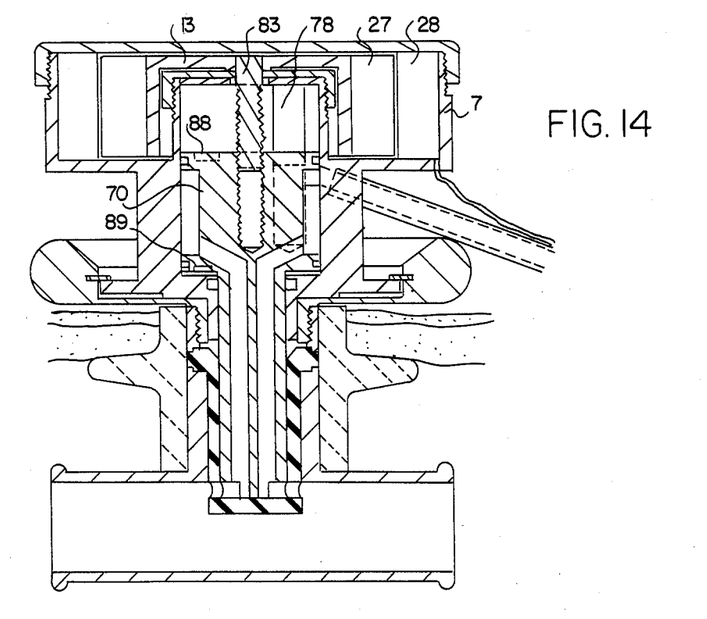

FIG. 14 shows another adaptation of the same connection head to an electric actuator. The head is this time in the low position, with the valve open.

The electric motor is in all points comparable to the motor of FIG. 7, but the rotor 7 acts directly on the threaded shaft 83. The travel of tubular body 9 is stopped when one of the electric contacts—not shown—is actuated by one or other flat face of piston 70, in the regions 88 or 89 for example which are recesses containing these electric contacts.

The connection head of the invention further comprises safety devices for preventing any false maneuver detrimental to the living organism. An explanation thereof requires reference to the preceding Figures.

Figures 1 to 4 show a valve position safety device. Since the elastomer valve 6 is inside the percutaneous passage and hidden by the connection head of the invention, it is impossible to see whether the valve is in a closed position, or, following malfunction, blocked in the open position or even broken. To avoid injecting aseptisizing fluids into the living organism, the safety device indicates the position of the valve.

This safety device is formed of a feeler 92, which passes through the tubular body 9 without friction and is in permanent contact with the end face 17 of the piston of valve 6. This contact is established under the effect of the thrust of a spring 96 which, at the head of the feeler 92, bears on a plug fixed to the connection head 12 on the one hand and to a washer 93, having an index 94, integral with the feeler 92 on the other. Of course, the force of spring 96 is calibrated so as not to open the valve by its thrust.

When valve 6 is closed, the length of rod 92 is such that the index 94 does not touch the top of piece 12: the aspetisizing fluid may then be caused to flow without danger.

If index 94 touched the top of piece 12 this would be the sign that the bottom of valve 6 were held in a low position, so a risk of communication between the aseptisizing liquid and the organism and would require checking.

When valve 6 is open and tubular body 9 in the low position, the index 94 of feeler 92 is in the high position, as is shown in FIGS. 2 and 3.

This mechanical safety device may be replaced by an electric safety device in the case where, as in FIG. 7, the actuator is an electric motor.

This electric safety device comprises parts common with the mechanical safety device: feeler 29, washer 93, spring 96, but an electric contact 33 indicates the position of feeler 92. In normal operation, when the tubular body 9 is in the high position and valve 6 closed, washer 93 must be half way. If it is at the end of travel, in the low position, and crushes the electric contact 33, that means that valve 6 is accidentally open: a simple logic circuit which combines contacts 33 (position of valve 6), contacts 30 (position of the tubular body 9) and an electromagnetic valve in the aseptisizing fluid circuit prevents flow of this aseptisizing fluid.

Figure 15:
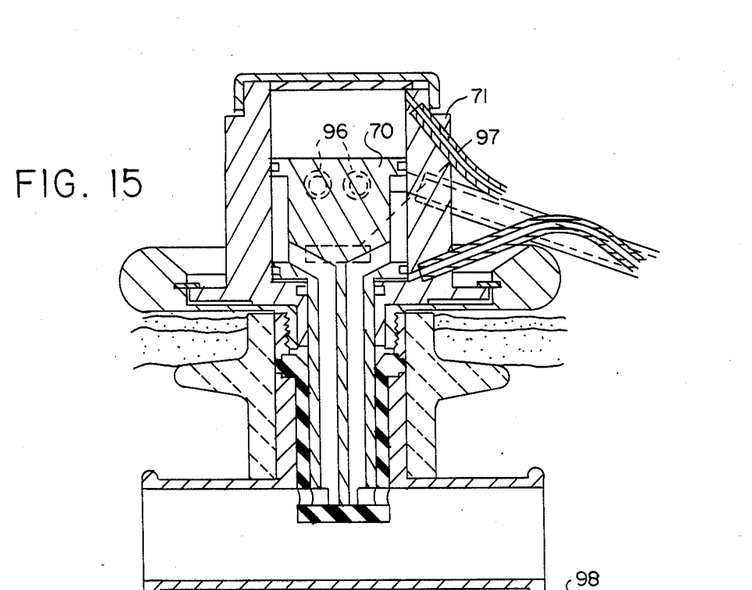
Figure 16:
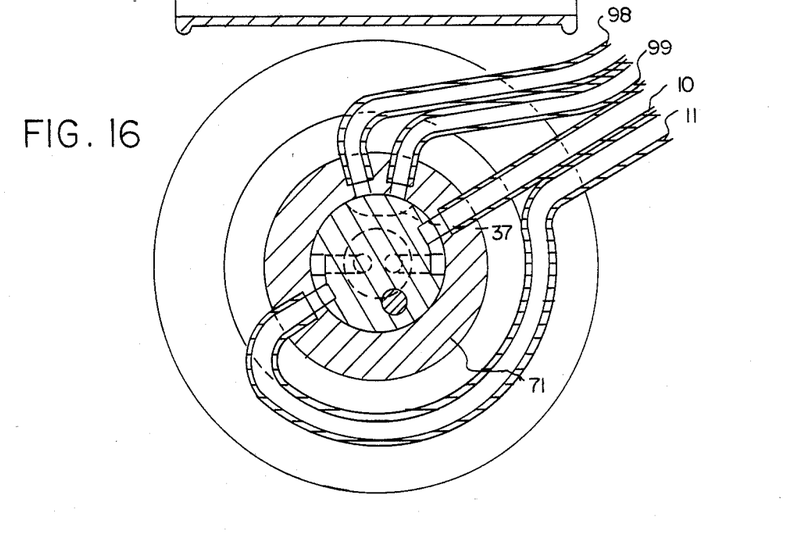

Finally, FIGS. 15 and 16 show a safety device installed directly in the aseptisizing fluid intake circuit. This safety device is particularly well adapted when the actuator of the connection head is a fluid actuator, comprising a piston 70. The aseptisizing fluid, before reaching one of the external tubes 10 and 11 passes through a bypass which is only open when the tubular body 9 is in the high position, so in the aseptisizing-rinsing-bubble removal position.

The aseptisizing fluid arrives through a pipe 98, for example which passes through the cylinder 71 of the actuator and it leaves, under the same conditions, through another pipe 91. The orifices of these two pipes referenced 96 emerge in correspondence with a groove 97 formed in the piston 70 of the actuator. When piston 70 is in the high position, groove 97 allows fluid to flow between the two pipes 98 and 99. When piston 70 is in the low position, with a valve open, groove 97 is no longer facing the orifices 96 and the wall of piston 70 closes them hermetically: the flow of aseptisizing fluid is impossible.

Finally, it was mentioned that the tubular body 9 comprises at least two channels 20 and 21—the other holes for feeler, screws, antirotation stud are not fluid flow channels—and the Figures only show two so as not to overload the drawings. However, the case where one or more additional channels are formed in the tubular body 9 falls within the scope of the invention. These channels may be used, for example, for injecting anticoagulants or medicaments at the same time as the blood is reinjected into the organism after treatment.

The materials for forming the connection head of the invention have not been mentioned up to now. All metal and/or plastic materials are suitable provided that the parts formed with these materials are aseptisizable and biocompatible is they are in contact with the blood or a fluid injected into the blood network, that the materials comply with the mechanical criteria which ensure reliability of the connection head, in particular proper sliding of the tubular body 9 in the guide cylinder 8, and the absence of corrosion in the presence of the fluids in contact with the different parts of the connection head.

One of the characteristic aspects of the invention is to guarantee an efficient flow of different fluids not only for aseptisiing the immovable percutaneous passage system before the beginning of treatment, but also for completely sweeping the tubes and cavities, so that traces of disinfectant or chemicals do not remain in the circuit when a treatment begins.

It is to obtain this fluid flow that the connection head of the invention is necessarily associated with a so called initial part, which belongs to the field of the invention, situated between the treatment apparatus—a dialyzer—and the connection head. This initial part is formed by a fluid distributor device whose characteristics is—as for the connection head—not to have any volume which cannot be swept by a moving fluid.

Figure 17:
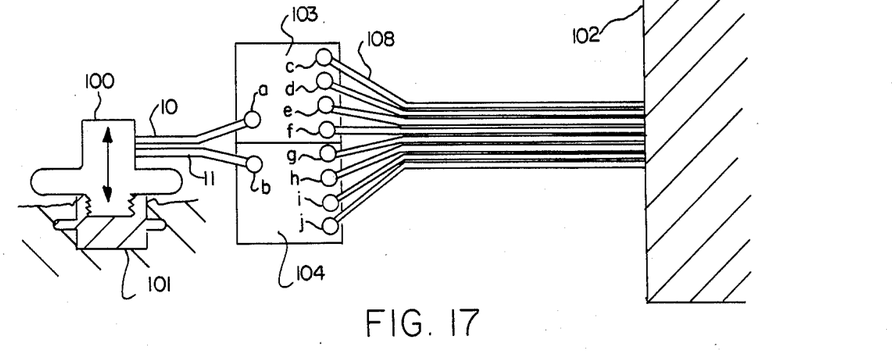

FIG. 17 shows a very simplified diagram of a treatment system, comprising a connection head 100, mounted on a percutaneous passage 101 implanted in a living organism, a distributor housing 103+104 and a fluid generation or treatment apparatus 102.

The distributor housing necessarily comprises two separate parts, each of which is connected to one of the two external tubes 10 and 11 of the connection head. By way of non limitative example, part 103 of the distributor housing is connected by connection "A" to tube 10 and corresponds to the introduction of fluid into the connection head 100, whereas part 104 is connected, through connection "b", to tube 11 and corresponds to the discharge of fluids coming from the connection head 100.

A plurality of tubes situated upstream correspond to the two tubes 10 and 11 situated downstream of the distributor housing 102+104. These tubes, connected to the housing by connections "c, d, . . . i, j", have flowing therethrough the different fluids delivered or absorbed by the treatment apparatus 102: disinfectant liquid, blood serum, medicamentous products . . . ; etc. It is therefore important for the inner volume of each part 103 and 104 of the distributor housing to be aseptisized and have the bubbles removed before treatment, just like the connection head, and not to have any unused volume which is not swept by a fluid.

In the simple cases, where there are only in housing 103 for example two upstream tubes—for example "c" and "d"—and a downstream tube 10, a three way plug valve is suitable, since it may connect "c to a" or "d to a" and because it comprises no unused space.

In the most general case, the one shown schematically in FIG. 17, simple valves must be used but mounted without harmful dead space. A non limitative example thereof is given in FIG. 18.

Figure 18:
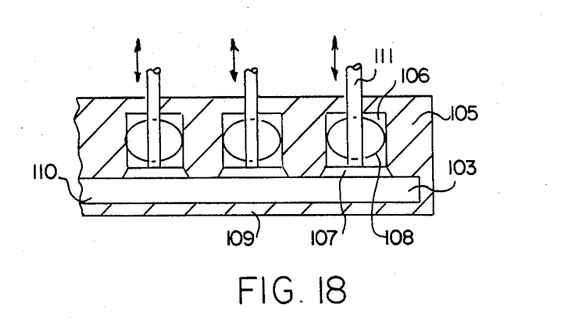

In FIG. 18 is shown a cavity 103, forming a half of the distributor housing, between a part 105 and a plate 109. Part 105 is machined so as to have formed therein a plurality of chambers 106, each closed on the cavity 103 side by a valve 107 and fed with fluid through a pipe orifice 108. The surface of cavity 103, closed by valves 107 and the surface of part 105, has no portion which is not swept by the fluids. Valves 107 correspond to the connections "c, d, e, f" of FIG. 17, and the free orifice 110 of cavity 103 is connected to an external tube 10 of the connection head 100. It may be noted that the fluids coming from cavity 103 to one of the valves c to f may, depending on the moment considered during a complex treatment such as kidney dialysis for example, either arrive at c and leave at a towards the connection head 100, or be interrupted, or else arrive at c and leave at d, e or f so as to accompany a fluid arriving at a. Thus, in the case of kidney dialysis, an anticoagulent injection may be made if required either towards head 100 or towards the apparatus 102 so as to protect the whole of the pipes from coagulation.

Valves 107 are operated from the outside, either manually, or by a mechanical, electric or fluid automatism: the longitudinal movement thereof causing opening or closing of a valve;

Of course, the distributor housing comprises fixing, connection or sealing means which are not shown so as to simplify the Figure.

In the case of FIG. 18, it is always advantageous for the least dangerous and the least coaguable fluid to be introduced or injected through the valve 111 which is situated at the end of the cul-de-sac. Thus, there cannot be prolonged stagnation of bloood or antiseptic liquid for example in this zone. Only rinsing liquid could stagnate, which is not troublesome.

The purpose of housings 103 and 104 and the integration thereof in the system comprising the connection head will appear even more clearly if we consider that the different aseptic, rinsing, bubble removal and possible anticoagulation operations related to the problem of connecting an external network to an internal network of a living organism must take place in the simplest, most flexible, most accurate and most rapid manner possible.

It follows from all these constraints that it is very advantageous for the total length of the circuit providing the successive fluid flows for aseptisizing, rinsing purposes, etc . . . , namely pipe 10 plus pipe 11 to be as short as possible. If such is the case, the respective amounts of fluids required for aseptisizing, rinsing, etc purposes . . . will be the lowest possible and the duration of the passage thereof will therefore be as short as possible. It is even possible to envisage, for certain complex operations such as kidney dialysis for example, a momentary fluid flow in a direction opposite to the usual direction.

The ideal implantation position for housing 103+104 will therefore be in the immediate vicinity of the connection head 100, although this remark in no way limits the invention.

For example, if the immovable percutaneous passage 101 is implanted in the arm of a patient, with the connection head 100 fixed above, housing 103+104 will be fixed to the same arm with a strap.

Tubes 10 and 11 connecting head 100 to housings 103 and 104 will necessarily be made from a fairly flexible material so that the mechanical forces, possibly not inconsiderable, caused by the connection to the housings 103 and 104 of the large bundle of pipes and wires coming from the heavy apparatus 102 cannot be transmitted to the connection head.

The presence of housings 103+104 on the body of the patient facilitates for him moreover the operation of the valves "a" to "j" which are fixed thereto in the case where they are manually controlled.

Of course, in the case of an overall apparatus for a complex operation such that kidney dialysis is partially or totally automated, the use of a connection head in accordance with the invention, having a fluid or electric control, with the use, in the immediate vicinity of a housing 103+104 of the invention itself comprising fluid or electric controls forms an assembly of indispensable arrangements which completes the assembly of the automated components contained in the treatment apparatus 102.

The invention is not limited to the forms or means described and shown. Equivalent forms, or different means but evident for one skilled in the art and whose use would not involve an inventive activity form part of the invention, whose scope is defined in the following claims.

What is claimed is:

1. A removable connection head for connection to an immovable percutaneous passage device giving access to the blood circuit of a living organism or to any zone of the organism this percutaneous passage comprising an access well formed by a cylindrical hollow body having a valve at one end closest to the patient and a threaded portion at the other end furthest from the patient, which connection head further comprises:
   means for fixing said head to the immovable device, these means being formed by a base whose central part, is formed as an extra thickness, which base is screwable on the hollow body and has an internal, hollow tubular guide cylinder coaxial with the hollow body,
   means for the exchange of fluids with the blood circuit, formed by: a tubular body fitting snugly into the guide cylinder, said tubular body having through the whole of its length at least two channels opening into the access well, which places the channels independently in communication with the blood circuit, and a connecting piece integral with the tubular body providing the connection between each of the channels and an external connection tube,
   means for actuating the head formed by an actuator which communicates to the tubular body, through the connecting piece, at least a longitudinal translational movement,
   means for operating the valve, said means positioned at the end of the tubular body close to the valve and being capable of providing interruption of a communication between the channels when the tubular body is in contact with the valve and, when this valve is open and is in communication with the blood circuit.

2. The connection head as claimed in claim 1, wherein the translational movement of the tubular body is capable of opening the valve and places the blood circuit in communication with the external tubes.

3. The connection head as claimed in claim 1, wherein the means for operating the valve is formed by a dividing wall, integral with the tubular body, placed between the orifices of the two channels, this tubular body providing a sealing contact with the walls of the access well and with the valve, when the tubular body is in a low position.

4. The connection head as claimed in claim 1, wherein the means for operating the valve is formed by the extension of one of the two channels with respect to the other channel, the extended channel being closed when it comes into contact with the surface at the bottom of the access well and simultaneously opening the valve.

5. The connection head as claimed in claim 1, wherein the actuator is a mechanical actuator, formed by an actuating nut held at a fixed distance with rrespect to the base, this actuating nut having a threaded portion which cooperates with a threaded portion carried by the connecting piece, rotation of the actuating nut imparting a longitudinal translational movement to the connection piece and to said tubular body and thereby opening or closing the valve.

6. The connection head as claimed in claim 1, wherein the actuator is an electric actuator, formed by a stator integral with a base and a rotor having a threaded portion which cooperates with a threaded portion carried by the connecting piece, rotation of the rotor imparting a translational movement to the connecting piece and to the tubular body and thereby opening or closing the valve.

7. The connection head as claimed in claim 6 further comprising an electric position safety device, formed by two electric contacts at the end of travel of the connecting piece furthest from the patient and by an electric position contact of the feeler, the combination of said contacts and a switching means permitting or preventing the operation of the electric motor in cooperation with an electrically powered motor.

8. The connection head as claimed in claim 1, wherein the actuator is a fluid actuator activated by a gas or a liquid, formed by a cylinder concentrically integral with the guide cylinder and by a piston, concentrically integral with the tubular body and forming a connecting piece, the cylinder of the fluid actuator being closed by a cover.

9. The connection head as claimed in claim 1, wherein the connecting piece is a piston, with smooth walls, fitting snugly into a cylinder through which connecting piece are connected the external connection tubes, the connection between the channels of said tubular body and said external tubes taking place through circular recesses or grooves formed in the wall of said cylinder.

10. The connection head as claimed in claim 1, wherein the connecting piece is a piston, fitting snugly into a cylinder through which are connected the external connection tubes, the connection between the channels of said tubular body and said external tube taking place through circular recesses or grooves formed parallel to the axis in the wall of the piston.

11. The connection head as claimed in claim 10 wherein, for providing good fluid flow in the grooves, these latter have a U-shaped cross section the length of two parallel grooves being equal to the translational length of the connecting piece.

12. The connection head as claimed in claim 10 further comprising a safety device this safety device being formed for a bypass of fluids, by means of two tubes connected to the cylinder in which the connecting piece moves, a groove in said connecting piece placing the orifices of said tubes in communication when the connecting piece is in a high position (valve closed), whereas the wall of the connecting piece closes said orifices when the connecting piece is in a low position (valve open).

13. The connection head as claimed in claim 1, further comprising a mechanical position safety device, formed by a feeler passing longitudinally through the connecting piece and the tubular body, this feeler being held in contact with the valve under the action of a spring within the connecting piece and having an index which indicates the position (open or closed) of the valve.

14. A fluid distribution housing providing connection between the external tubes of the connection head as claimed in claim 1, and a plurality of tubes connected to a treatment apparatus, said housing containing as many sealed chambers as tubes which are connected to the connection head and each of said sealed chambers having as many valves without dead space as there are tubes which are connected thereto.

15. The fluid distribution housing as claimed in claim 14, situated in the immediate vicinity of the connection head and connected thereto by flexible connections only.

16. The housing as claimed in claim 14, wherein all the valve operations can be effected manually.

17. The housing as claimed in claim 14, wherein all the valve operations can be effected by electromagnetic, electric or fluid control obeying, as well as the electric or fluid control of the connection head, and a sequencer completely automating the operation for treating the fluid concerning the organism.

18. The fluid distribution housing as claimed in claim 14, wherein the valves without dead space are formed by valve parts flush with the wall of the cavity of the housing.

19. A removable fluid supply system for connection to an immovable percutaneous passage apparatus giving access to the fluid circuit of a living organism, comprising:
an initial part formed by a fluid distribution housing, as claimed in claim 14, and
a terminal part formed by a head for connection to a percutaneous passage.

* * * * *